(12) United States Patent
Ozgur et al.

(10) Patent No.: US 12,196,982 B2
(45) Date of Patent: *Jan. 14, 2025

(54) DOG BONE SHAPED CYLINDRICAL TUNABLE FLUIDIC LENS WITH MINIMIZED DEFOCUS

(71) Applicants: ARIZONA BOARD OF REGENTS ON BEHALF OF THE UNIVERSITY OF ARIZONA, Tucson, AZ (US); iCRx, Inc., Tucson, AZ (US)

(72) Inventors: Erol Ozgur, Tucson, AZ (US); Daniel Reetz, Tucson, AZ (US); Farhad Akhoundi, Tucson, AZ (US); Gholam Peyman, Tucson, AZ (US)

(73) Assignees: ARIZONA BOARD OF REGENTS ON BEHALF OF THE UNIVERSITY OF ARIZONA, Tucson, AZ (US); ICRX, INC., Tucson, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/326,926

(22) Filed: May 31, 2023

(65) Prior Publication Data

US 2023/0305195 A1  Sep. 28, 2023

Related U.S. Application Data

(62) Division of application No. 17/100,133, filed on Nov. 20, 2020, now Pat. No. 11,703,617.

(51) Int. Cl.
  *G02B 3/14*    (2006.01)
  *A61B 3/028*   (2006.01)
  (Continued)

(52) U.S. Cl.
  CPC .............. *G02B 3/14* (2013.01); *A61B 3/0285* (2013.01); *A61B 3/04* (2013.01); *G02B 3/06* (2013.01);
  (Continued)

(58) Field of Classification Search
  CPC ........... A61B 3/0285; G02B 3/12; G02B 3/14
  (Continued)

(56) References Cited

U.S. PATENT DOCUMENTS 2,051,791 A * 8/1936 Luce ................ G02B 3/12
                                                              359/666
2,836,101 A * 5/1958 Jan ................. G02B 3/14
                                                              359/666

(Continued)

OTHER PUBLICATIONS

M. Stürmer, A. Schatz and U. Wallrabe, "Cylindrical lens with integrated piezo actuation for focal length tuning and lateral scanning," 2014 IEEE 27th International Conference on Micro Electro Mechanical Systems (MEMS), 2014, pp. 1171-1174, doi: 10.1109/MEMSYS.2014.6765855 (Year: 2014).*

(Continued)

*Primary Examiner* — Zachary W Wilkes
(74) *Attorney, Agent, or Firm* — NGUYEN TARBET IP LAW

(57) ABSTRACT

The invention relates to cylindrical tunable fluidic lenses. The cylindrical optical power of the lenses may be continuously tuned within at least ±10 diopters, without inducing any significant spherical aberration, or any other significant aberrations. The lenses feature a geometry that produces minimal or no spherical defocus. These cylindrical tunable fluidic lenses could be used to induce and/or correct cylindrical optical aberrations in adaptive optical systems, particularly in ophthalmologic applications related to objective and automatic assessment of the refractive error of the eye, without the need of receiving feedback from the subjects.

1 Claim, 16 Drawing Sheets
(7 of 16 Drawing Sheet(s) Filed in Color)

(51) Int. Cl.
*A61B 3/04* (2006.01)
*G02B 3/06* (2006.01)
*G02B 3/00* (2006.01)
*G02C 7/02* (2006.01)

(52) U.S. Cl.
CPC ...... *G02B 2003/0093* (2013.01); *G02C 7/022* (2013.01)

(58) Field of Classification Search
USPC .......................................... 359/666; 351/227
See application file for complete search history.

(56) References Cited

U.S. PATENT DOCUMENTS

| | | | | | |
|---|---|---|---|---|---|
| 3,161,718 | A | * | 12/1964 | De Luca | G02B 1/06 92/96 |
| 5,233,470 | A | * | 8/1993 | Wu | G02B 3/12 359/896 |
| 5,684,637 | A | * | 11/1997 | Floyd | G02C 7/085 359/666 |
| 5,973,852 | A | * | 10/1999 | Task | G02B 3/14 359/666 |
| 6,188,525 | B1 | * | 2/2001 | Silver | G02B 3/14 359/666 |
| 7,413,306 | B2 | * | 8/2008 | Campbell | G02B 26/004 359/666 |
| 7,436,598 | B2 | * | 10/2008 | Kuiper | G11B 7/1376 |
| 7,826,146 | B2 | * | 11/2010 | Campbell | G02B 26/004 359/666 |
| 9,016,860 | B2 | * | 4/2015 | Peyman | A61F 2/1635 351/200 |
| 9,191,568 | B2 | * | 11/2015 | Peyman | A61F 2/1648 |
| 9,671,607 | B2 | * | 6/2017 | Peyman | G02B 7/28 |
| 11,703,617 | B2 | * | 7/2023 | Ozgur | A61B 3/1015 351/235 |
| 2006/0007397 | A1 | * | 1/2006 | Lai | A61B 3/0285 351/205 |
| 2010/0142059 | A1 | * | 6/2010 | Chou | G02B 3/14 359/666 |

OTHER PUBLICATIONS

Erol Ozgur, Daniel Reetz, Farhad Akhoundi, Nicholas O'Brien, Jaclyn Wycoff, Ram Voorakaranam, Pierre-Alexandre Blanche, Lloyd LaComb, Chen Liang, Gholam Peyman, and N. Peyghambarian, "Parametric dog-bone-shaped tunable cylindrical fluidic lens," Appl. Opt. 60, 4755-4761 (2021) (Year: 2021).*

* cited by examiner

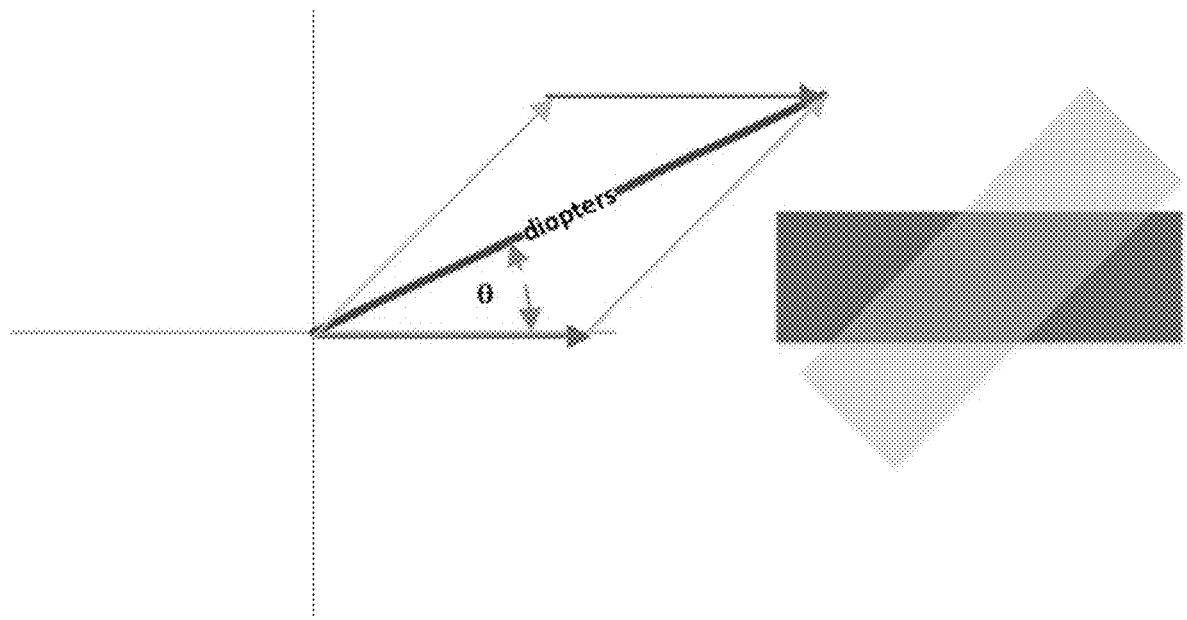

FIG. 7

| n | m | Z# | Polynomial | Aberration |
|---|---|----|----|----|
| 0 | 0 | 0 | 1 | *Piston* |
| 1 | 1 | 1 | $\rho \cos\theta$ | *Tilt x* |
|   |   | 2 | $\rho \sin\theta$ | *Tilt y* |
|   | 0 | 3 | $2\rho - 1$ | Defocus, *Piston [This term corrects for focal errors in the eye]* |
| 2 | 2 | 4 | $\rho \cos 2\theta$ | Astigmatism, Defocus |
|   |   | 5 | $\rho \sin 2\theta$ | Astigmatism, Defocus |
|   |   |   |   | *The two terms above correct for Astigmatism – there is a simple transformation to ophthalmic astigmatism* |
|   | 1 | 6 | $(3\rho - 2)\rho \cos\theta$ | Coma, *Tilt x* |
|   |   | 7 | $(3\rho - 2)\rho \sin\theta$ | Coma, *Tilt y* |
|   | 0 | 8 | $6\rho - 6\rho + 1$ | Spherical Aberration, Defocus |

FIG. 8

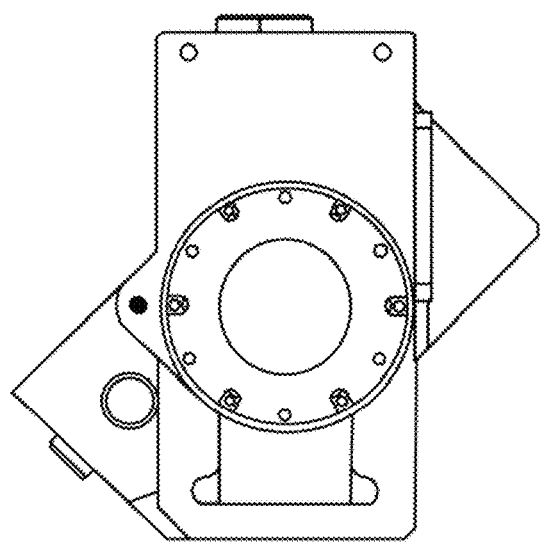 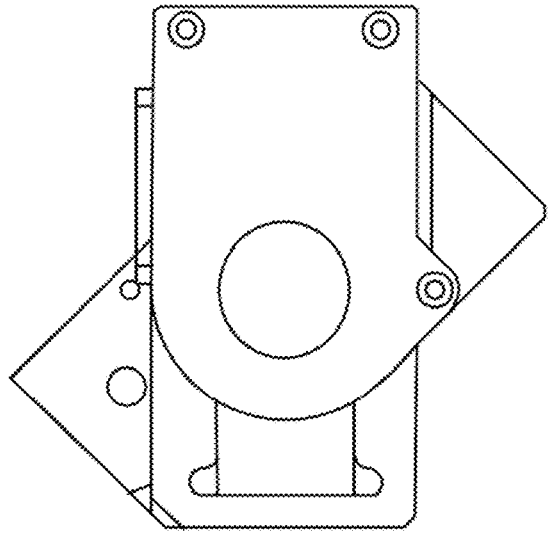
FIG. 19A  FIG. 19B
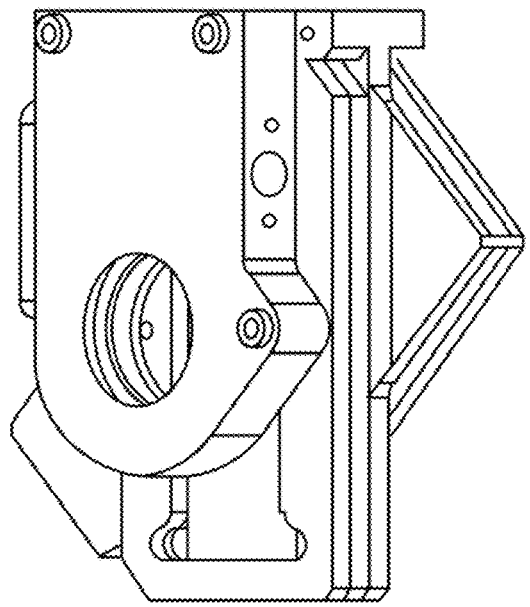 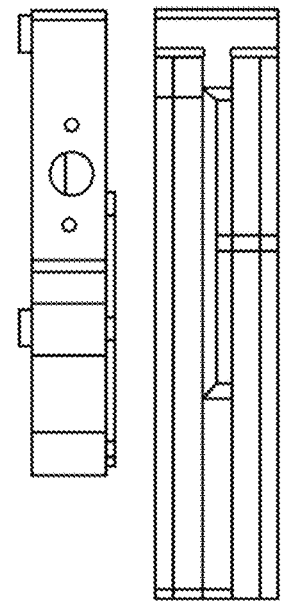
FIG. 19C  FIG. 19D

| Spec | Laser Liquid | Light Mineral Oil | Sonneborn 40 Oil | Sigma M1180 |
|---|---|---|---|---|
| Viscosity | 400cst | 30-200cst | 40cst | 34.7cst |
| Refractive Index | 1.53 | ~1.4 to 1.48 | 1.45 | 1.467 |
| Abbe Number | Vd 33.2 | Unknown | Unknown | Unknown |
| Density | 0.92g/cm^3 | 0.8g/cm^3 | 0.81g/cm^3 | .81-.89g/cm^3 |
| Pour Point | < 0C | <-10 to 5C | < 3C (40F) | Unknown |

DOG BONE SHAPED CYLINDRICAL TUNABLE FLUIDIC LENS WITH MINIMIZED DEFOCUS

BACKGROUND OF THE INVENTION

Field of the Invention

The present invention relates to tunable fluidic lenses. More specifically, the present invention relates to "dog bone" shaped tunable fluidic lenses with cylindrical optical power and minimal distortion.

Background Art

Tunable lenses are used in many optical applications such as imaging, beam manipulation, and medical devices. Tunable fluidic lenses exploit the change in the shape of a membrane that occurs when a fluid exerts a force on the membrane. The shape of the deformed membrane refracts the light as a glass lens does, with the advantage that the focal length can be tuned according to the pressure differential across the membrane.

To change the refractive characteristics of a tunable fluidic lens, a fluid (such as a transparent liquid) is confined within a container that has at least one face made of a flexible and transparent material (or membrane), and the pressure differential between the outside fluid (e.g. the atmosphere) and the internal fluid causes the flexible face to curve inward or outward. The magnitude of this curvature is correlated with the amount of pressure and the flexibility of the membrane. The geometry of the lens' open face or faces determines the light refraction characteristics of the lens. For example, a circular flexible open face corresponds to a spherical lens, which could be tuned to be either a convex (positive) or a concave (negative) lens with various optical power and focal length.

An optical wavefront may be fully mathematically defined as the sum of physical characteristics related to the position of the light waves having the same phase at a given time, such as tip/tilt, defocus, and astigmatism. All these characteristics are independent from each other, and they may be described by orthonormal mathematical notations, named Zernike polynomials. Zernike polynomials are a complete basis set in two variables ($\theta$ and $p$) that are orthogonal in continuous fashion over the unit circle. Defocus and astigmatism are among the most common optical aberrations, particularly encountered in ophthalmology as refractive errors. Spherical tunable fluidic lenses may be effectively used to correct the defocus, and are being used in both scientific and medical applications. Cylindrical counterparts, on the other hand, have not yet fully emerged. In previous reports related to cylindrical fluidic lenses, rectangular apertures (instead of circular) are used to cause a cylindrical contribution in the fluidic lens. However, with this rectangular aperture, the fluidic lens shows not only the desired cylindrical component, but also spherical defocusing, and other aberrations (i.e. higher order Zernike terms) (See Marks et al, "Astigmatism and defocus wavefront correction via Zernike modes produced with fluidic lenses", APPLIED OPTICS/Vol. 48, No. 19/1 Jul. 2009, pp 3580-3587). This introduces a complication in the application, requiring this spherical defocus effect to be compensated by another tunable lens devoted to correcting the defocus introduced by the cylindrical lens. Wedge-shaped edges have been suggested to reduce the defocus cylindrical lenses; however, the wedge parameters have not been fully characterized in detail or optimized.

The underlying reason for the spherical defocus of the rectangular cylindrical lenses is that for a perfect cylindrical lens shape, the length of the rectangle should be much larger than its width. Therefore, a high aspect ratio is required to fabricate a cylindrical tunable fluidic lens with minimal defocus or other aberrations. However, this results in a bulky structure, which is impractical to fabricate. Therefore, instead of fluidic cylindrical lens, a set of rigid cylindrical lenses with variable optical power that depends on the rotation (which require complex and inconvenient mechanical systems to control their rotation precisely) have been previously proposed for commercial applications.

A cylindrical tunable fluidic lens should possess the following characteristics to have an effective use related to manipulation and correction of the cylindrical aberration of the wavefront:

1. The lens should use the same simple operation principles as tunable spherical fluidic lenses. No additional optical and mechanical components should be necessary.
2. The lens should provide insignificant, in any, spherical contribution to the wavefront.
3. The lens should be of comparable size to spherical fluidic lenses.
4. The lens should not induce non-cylindrical aberrations on the optical wavefront.

BRIEF SUMMARY OF THE INVENTION

It is an objective of the present invention to provide systems, devices, and methods that allow for tunable fluidic lenses that cause purely cylindrical focusing, as specified in the independent claims. Embodiments of the invention are given in the dependent claims. Embodiments of the present invention can be freely combined with each other if they are not mutually exclusive.

The present invention features cylindrical tunable fluidic lenses which do not have significant spherical contribution to the resulting wavefront, and may be used over a range of cylindrical optical power without the need to compensate for resulting spherical defocus effects or higher order aberrations. The lenses are simple and compact, and may have a relatively low length to width ratio for a cylindrical lens. Like spherical tunable fluidic lenses, the lenses of the present invention utilize a fluid chamber which is in contact with at least one flexible membrane which may be deformed by a change of the relative pressure across the membrane. Unlike previously proposed cylindrical tunable fluidic lenses, the effective shape of the flexible membrane is not a simple rectangle.

One of the unique and inventive technical features of the present invention is the use of a dog bone shaped opening such that the flexible membrane of a fluidic lens may be deformed in a dog bone shape. Various examples of dog bone shapes are provided herein, all of which have a relatively narrow center region which connects two wider end regions. Without wishing to limit the invention to any theory or mechanism, it is believed that the technical feature of the present invention advantageously and surprisingly provides for the lens to function as a tunable cylindrical lens, without causing spherical defocusing effects or non-cylindrical aberrations. None of the presently known prior references or work has the unique inventive technical feature of the present invention. Furthermore, the prior references teaches away from the present invention.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE SEVERAL VIEWS OF THE DRAWINGS

The patent application or application file contains at least one drawing executed in color. Copies of this patent or patent application publication with color drawing(s) will be provided by the Office upon request and payment of the necessary fee.

The features and advantages of the present invention will become apparent from a consideration of the following detailed description presented in connection with the accompanying drawings in which:

FIG. 4A shows an example in which a lens is assembled such that the dog bone shaped frame geometrically limits the stretching of the flexible transparent membrane below it. The reservoir has another membrane that may be pushed or pulled so as to induce fluid flow through the connection channel. FIG. 4B shows the assembly of two such cylindrical lenses together to correct for any angle of astigmatism. In this example the two lenses share an optical window, so their flexible faces are oriented on opposite sides.

FIG. 5A shows a rectangular shaped cylindrical lens, FIG. 5B shows an oval shaped cylindrical lens, and FIG. 5C shows a dog bone shaped cylindrical lens. These shapes were evaluated using Finite Element Analysis (FEM) for different geometries, constructing an elastic fluidic lens face, and investigating the longitudinal flatness of each shape through FEM simulations. The geometry that shows the smallest deviation from a flat profile along the x-axis is selected for fabrication, as shown in the FIGS. 5A-5C.

FIG. 6A shows the case where P1 is equal to P2 and the membrane remains flat, with no deformation, such that light passing through the lens (parallel arrows) is unaffected by the lens. FIG. 6B shows the case where P1 is less then P2 and the membrane is deformed by the pressure difference such that light passing through the lens converges to the center of the beam. FIG. 6C shows the case where P1 is greater than P2 and the membrane is deformed by the pressure difference such that light passing through the lens diverges from the center of the beam.

FIG. 7 illustrates the vector decomposition of astigmatism. Astigmatism has a magnitude (diopters) and an angle, (axis) and can be decomposed into two non-colinear sub vectors based on the axes of two offset cylindrical lenses. In this example, the two cylindrical lenses are offset such that the center point of the two lenses are aligned and one of the lenses is rotated relative to the other.

FIG. 8 shows a table of Zernike polynomials corresponding to the types of aberrations often observed in optical tests, including defocus, astigmatism, and spherical aberration.

FIG. 19A shows a front view illustration of a fluidic lens assembly of the present invention.

FIG. 19B shows a front view illustration of another fluidic lens assembly of the present invention.

FIG. 19C shows a perspective view illustration of a fluidic lens assembly of the present invention.

FIG. 19D shows a side view illustration of a fluidic lens assembly of the present invention.

DETAILED DESCRIPTION OF THE INVENTION

Figure 1:
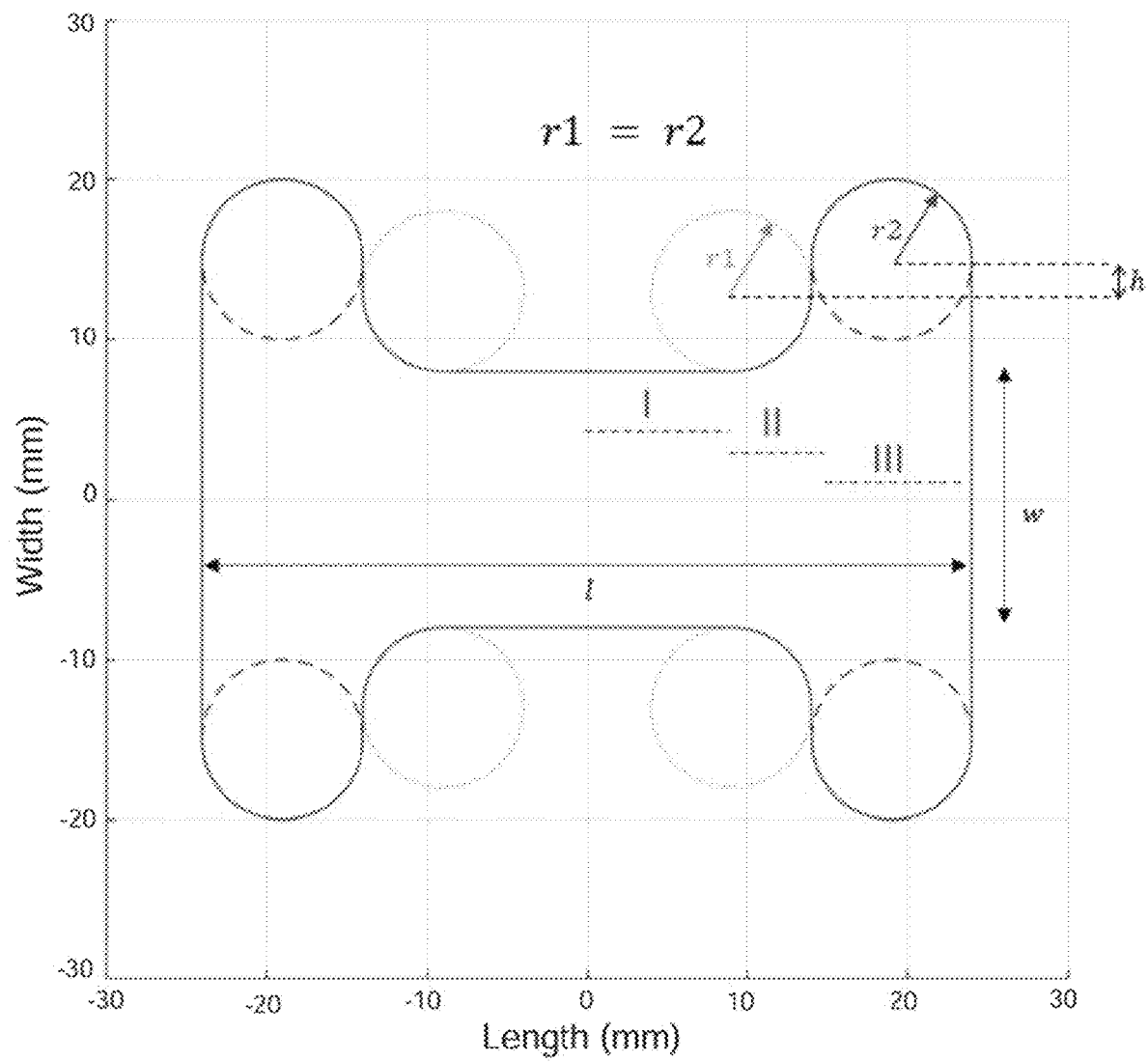
FIG. 1 shows a parametric dog bone geometric design of the present invention. The basic parameters used in the design are shown in the image. Two auxiliary circles are used at each corner to define the inward and outward curvature of the dog bone shape. In this example, the circles have the same radius. The second circle is a height (h) higher than the first. Three separate calculation regions (I, II, and III) are shown in the figure.

Following is a list of elements corresponding to a particular element referred to herein:
- 100 First cylindrical fluidic lens
- 102 Fluidic chamber
- 110 Reservoir body
- 112 Membrane assembly
- 120 Inner membrane retainer
- 130 Membrane
- 140 Outer membrane retainer
- 150 Internal window
- 152 Fill port
- 160 Purge port
- 170 Pump
- 200 Second cylindrical fluidic lens
- 202 Fluidic chamber
- 212 Membrane assembly
- 220 Inner membrane retainer
- 230 Membrane
- 240 Outer membrane retainer
- 252 Fill port
- 260 Purge port
- 300 Spherical fluidic lens
- 352 Fill port
- 360 Purge port
- 400 Fluidic lens assembly In one embodiment, the present invention features a cylindrical fluidic lens. Preferably, the lens is tunable over a range of optical power. As a non-limiting example, the cylindrical fluidic lens may comprise a fluidic chamber having an opening and a flexible transparent membrane attached to the fluidic chamber and covering the opening. In some embodiments, a power of the cylindrical fluidic lens may be based on a deformation of the flexible transparent membrane, and the deformation and power are configured to change based on a pressure difference between the fluidic chamber and the other side of the flexible transparent membrane.

In some embodiments, the flexible transparent membrane may be deformed by higher pressure inside the fluidic chamber than outside the fluidic chamber, such that a surface of the flexible transparent membrane forms a convex shape. In other embodiments, the flexible transparent membrane may be deformed by lower pressure inside the fluidic chamber than outside the fluidic chamber, such that the surface of the flexible transparent membrane forms a concave shape. In still other embodiments, when the pressure inside the fluidic chamber may be equalized with the pressure outside the fluidic chamber such that the flexible transparent membrane is substantially flat, and the lens has substantially zero optical power. In some embodiments, the greater the pressure difference across the membrane, the greater the magnitude of the optical power of the lens.

According to one embodiment, the opening may have a dog bone shape. As used herein, the term "dog bone shape" refers to a continuous shape which has a narrow center region which connects two wider end regions. For ease of reference, the respective sides of a dog bone shape are referred to herein as "left," "right," "top," and "bottom" sides, but the shape may be positioned in any orientation (for example, such that the "horizontal" sides are vertical or diagonal in orientation). The terms "left," "right," "top," "bottom," "vertical," "horizontal," "upper," and "lower" indicate direction and position relative to each other, but not to any particular external frame of reference. For example, if a rectangle is rotated clockwise by 90 degrees, the upper left and lower right corners may end up in the upper right and lower left positions respectively. A cylindrical tunable fluidic lens with a dog bone shape may avoid optical aberration other than astigmatism. The dog bone geometry enables the fabrication of a perfect cylindrical lens via fine-tuning of the shape parameters.

As a non-limiting example, the dog bone shape may comprise: a rectangular region, having a width, a height, four corners, and a center axis running from a left side of the rectangular region to a right side of the rectangular region; and a rounded protrusion extending vertically from each corner of the rectangular region, wherein each rounded protrusion comprises a concave curve around a first auxiliary ellipse and a convex curve around a second auxiliary ellipse. Counting the two auxiliary ellipses at each corner, the shape may trace along a total of 8 or more ellipses. The edge of each rounded protrusions may extend vertically from each corner and then curve towards the center of the shape so as to taper into the top or bottom side of the rectangular region. The rounded protrusions may additionally include a straight trace connecting the concave and convex curves, which is tangent to each of the two auxiliary ellipses. In some embodiments, one or more of the ellipses may comprise a circle. In other embodiments, each of the ellipses may be positioned such that the long axis of the ellipse is parallel to, perpendicular to, or at an angle to the long axis of the rectangular region. In some embodiments, the positions of the auxiliary ellipses (and thus the resulting shape) may be symmetrical about both vertical and horizontal axes.

In one embodiment, the invention features a cylindrical fluidic lens which includes a fluidic housing having an opening to a fluidic chamber, the opening having a dog bone shape; and a flexible transparent membrane attached to the fluidic chamber and covering the opening. In some embodiments, a power of the cylindrical fluidic lens may be based on a deformation of the flexible transparent membrane, and the deformation and power may be configured to change based on a pressure difference between the fluidic chamber and the other side of the flexible transparent membrane. In one embodiment, the ratio of a maximum length (along the long axis) and a minimum width (at the narrow center region) of the dog bone shape may be about 3:1. In alternative embodiments, the ratio may be less than about 1:1, 1.5:1, 2:1, 2.5:1, 3:1, 3.5:1, 4:1, 4.5:1, 5:1, 6:1, 7:1, 8:1, 9:1, or 10:1.

In preferred embodiments, the cylindrical fluidic lens of the present invention lacks significant spherical defocus and does not introduce significant higher order aberrations. For example, the cylindrical fluidic lens may have a maximum spherical defocus of less than 0.5 diopter. Furthermore, the cylindrical fluidic lens may have less spherical defocus than a rectangular shaped cylindrical fluidic lens of similar dimensions as the dog bone shaped lens. In one embodiment, the parameters of the dog bone shape may be optimized so as to minimize the spherical defocus and/or the introduction of higher order aberrations of the lens.

As one non-limiting example, the dog bone shape may include: a center rectangular region, having a constant width, a constant height, and a center axis running from a left side of the center rectangular region to a right side of the center rectangular region; a left end region, connected with the left side of the center rectangular region, having a maximum height that is greater than the height of the center rectangular region; and a right end region, connected with the right side of the center rectangular region, having a maximum height that is greater than the height of the center rectangular region.

As a second non-limiting example, the dog bone shape may include: an upper horizontal trace; an upper right concave trace, connected with the upper horizontal trace; an upper right convex trace, connected with the upper right concave trace; a right vertical trace, connected with the upper right convex trace; a lower right convex trace, connected with the right vertical trace; a lower right concave trace, connected with the lower right convex trace; a lower horizontal trace, connected with the lower right concave trace; a lower left concave trace connected with the lower horizontal trace; a lower left convex trace, connected with the lower left concave trace; a left vertical trace, connected with the lower left convex trace; an upper left convex trace, connected with the left vertical trace; and an upper left concave trace, connected with the upper horizontal trace. In some embodiments, the upper and lower horizontal traces may be straight and parallel. In other embodiments, the left and right vertical traces may be straight and parallel. In still another embodiment, the dog bone shape may additionally include a plurality of straight height-extension traces between the concave and convex traces of each corner.

In some embodiments, a fluidic lens of the present invention may additionally include a fluidic pump for changing a fluid pressure within the fluidic chamber. This change in fluid pressure may allow for control of the optical power of the lens. As a non-limiting example, the fluidic pump may generate a high fluid pressure, resulting in a high deformation and a large optical power, or may generate a lower fluid pressure, resulting in a lower deformation and a smaller optical power. In some embodiments, the fluidic lens may additionally include a fluid reservoir, separate from the fluidic chamber, which is connected with the fluidic chamber via tubes, channels, or some other fluidic connection. The fluidic pump may be fluidly connected with either the fluidic chamber, the fluidic reservoir, or with both. Non-limiting examples of pumps which may be suitable for use with the fluidic lenses of the present invention include, piston, plunger, peristaltic, diaphragm, gear, flexible-impeller, nutating, centrifugal, propeller, and screw pumps. Each of the fluidic lenses of the present invention may include a fill port and a purge port so as to allow for addition of fluid into the fluidic chamber of the lens and the removal of air from the fluidic chamber.

According to one alternative embodiment, a fluidic lens of the present invention may have two fluidic chambers, with a flexible membrane situated in an opening between the chambers so as to keep the fluids (i.e. liquids or gasses) from mixing. The shape of the opening between the chambers may be a dog bone shape. In preferred embodiments, the fluids in each chamber have different refractive indices. This may be accomplished by using totally different fluids or by using the same base fluid with different concentrations or doping reagents. Fluidic pumps may adjust the pressure within either or both fluidic chambers so as to change the pressure differential between the fluidic chambers and thereby change the deformation of the flexible membrane and the optical characteristics of the lens. Each of the chambers would preferably have an additional opening opposite from the shared opening which is sealed by a rigid or flexible transparent material, such that light may pass through both fluidic chambers of the lens and the flexible membrane between them.

In one embodiment, any of the lenses of the present invention may be part of an automated or manually operated system for correcting low order and high order aberrations of refractive errors. As a non-limiting example, the lens may be part of a fluidic lens system, which has two or more such fluidic lenses which are rotated about a shared center point of the cylindrical lenses, and thus offset from each other by an offset angle. The fluidic lens system may include both spherical and cylindrical fluidic lenses. As non-limiting examples, the offset angle between two cylindrical fluidic lenses may be about 1-15, 15-30, 30-45, 45-60, 60-75, or 75-90 degrees. In some embodiments, the offset angle between two cylindrical fluidic lenses may be about 45 or 90 degrees. Without wishing to limit the present invention to any particular theory or invention, positioning the lenses with such an offset angle may allow for two tunable cylindrical lenses, working in combination to correct for any axis of astigmatism. From a mathematical perspective, the optimal offset angle between the two cylindrical fluidic lenses may be 90 degrees, such that their axes are independent of each other. However, in some embodiments (for example, a phoropter system), it may be desirable to use an angle such as 45 degrees so as to open up a larger space between the lenses for a user's nose to fit, an thus provide better ergonomics. Without wishing to limit the present invention to any particular theory or mechanism, it is believed that with an offset angle of 45 degrees, the two cylindrical lenses are orthogonal in terms of Zernike polynomials and therefore may be used to correct all cylindrical aberrations, regardless of the cylindrical axis.

According to some embodiments, multiple lenses in a system may be designed and arranged so as to minimize the size of the system. As a non-limiting example, the lenses may be designed with relatively small aspect ratios for cylindrical lenses. As another non-limiting example, the lenses may be positioned back-to-back. As used herein, the term "back," refers to the side of the lens opposite of the lens' respective flexible transparent membrane. In one embodiment, two tunable fluidic lenses may be stacked together such that they share a transparent optical window. Additionally, the pump or fluid reservoir may share the main lens body or be positioned remotely and connected via tubing to save space.

In some embodiments, use of the tunable dog bone shaped cylindrical lenses of the present invention instead of tunable rectangular shaped cylindrical lenses may allow for miniaturization by nature of allowing for use of a greater portion of the lens area. Without wishing to limit the limit the present invention to any particular theory or mechanism, it is believed that a tunable rectangular shaped cylindrical lens may only have a usable area of about 75% of its total area, with the remainder of the area (e.g. at the edges of the lens) causing aberration. In contrast, a comparable tunable oval shaped cylindrical lens may have a usable area of about 80% of its total area, and a comparable tunable dog bone shaped cylindrical lens may have a usable area of about 95% of its total area. In alternative embodiments, a lens of the present invention may have a usable area greater than about 80, 81, 82, 83, 84, 85, 86, 87, 88, 89, 90, 91, 92, 93, 94, 95, 96, 97, 98, or 99 percent of its total membrane area.

In some embodiments, the tunable cylindrical lenses of the present invention may have radiused edges. As a non-limiting example, the radiused edge may be formed via fileting, polishing, burnishing, swaging, etching, electroplating, or other similar processes. In preferred embodiments, these radiused edges may allow the membrane to extend, contract, and stretch without cutting or damaging the membrane.

According to some embodiment, the present invention features a phoropter having a line of sight. In some embodiments, the line of sight may be for a viewer to see an eye chart. As a non-limiting example, the phoropter may include a tunable defocus lens in the line of sight, a first tunable astigmatic lens in the line of sight, and a second tunable astigmatic lens in the line of sight. In some embodiments, the first tunable astigmatic lens has a first cylindrical axis and the second tunable astigmatic lens has a second cylindrical axis which is offset by an offset angle from the first cylindrical axis. In preferred embodiments, each of the tunable astigmatic lenses lacks significant spherical defocus. The phoropter may include only a single fluidic lens assembly, or more preferably, may include separate fluidic lens assemblies for each of the left and right eyes of a user. The left and right fluidic lens assemblies may be mirror image versions of each other so as to ergonomically fit around the nose of the user.

In one embodiment, the tunable defocus lens comprises a spherical fluidic lens. In another embodiment, each of the tunable astigmatic lenses is a cylindrical fluidic lens which has a fluidic chamber with a dog bone shaped opening, and a flexible transparent membrane attached to the fluidic chamber and covering the opening. In some embodiments, change of the fluid pressure within the fluidic chamber may change the deformation of the flexible transparent membrane and thus the power of the tunable astigmatic lens.

As a non-limiting example, the dog bone shape may feature: a center rectangular region, having a constant width, a constant height, and a center axis running from a left side of the center rectangular region to a right side of the center rectangular region; a left end region, connected with the left side of the center rectangular region, having a maximum height that is greater than the height of the center rectangular region; and a right end region, connected with the right side of the center rectangular region, having a maximum height that is greater than the height of the center rectangular region.

In some embodiments, the dog-bone shape may be defined by curvature around a plurality of auxiliary ellipses. In addition to the curved traces along the auxiliary ellipses, the shape may include straight traces which connect the curved traces. Thus, the size, number, position, and ellipticity of the auxiliary ellipses may determine the shape, as well as the optical properties of the lens. The defocus characteristics of the lens may be fine-tuned by changing the parameters of the parametric dog bone equations, such as the size, number, position, and ellipticity of the ellipses and the length of the straight and curved traces. In preferred embodiments, the shape is symmetrical along both major and minor axes. The dog bone shape may be that of a continuous and smooth function, for example, a continuous and smooth piecewise function. Without wishing to limit the present invention to any particular theory or mechanism, it is believed that smoothness of the shape may avoid pinching or wrinkling of the membrane as well as the introduction of higher order aberrations.

In one embodiment, a phoropter of the present invention may also have wavefront sensors configured to detect local tilts of light wavefronts emerging from the eye. In some embodiments, the wavefront sensors may generate output signals for controlling the shape or focal length of at least one of the lenses. In other embodiments, the phoropter may also include one or more holographic or diffractive elements for collecting light scattered from an eye of the viewer and imaging the scattered light to the wavefront sensors.

The cylindrical tunable lenses of the present invention may be fabricated using methods which are similar to previous tunable fluidic lens fabrication methods. As a non-limiting example, the fabrication method may include 3D-printing, milling, molding to yield the desired shape.

The following is a non-limiting example of a fabrication method for the cylindrical tunable lenses of the present invention:

Step 1: Stretch and fix membrane between two retainers.
Step 2: Glue internal window into reservoir body.
Step 3: Sealed membrane assembly to reservoir body using gasketing sealant.
Step 4: Fasten membrane assembly into place on reservoir body.
Step 5: (Optional) Repeat operations for second cylindrical lens.
Step 6: Attach fill ports and purge ports to reservoir body.
Step 7: Connect lens or lenses to pump.
Step 8: Fill lens or lens assemblies with fluid.
Step 9: Purge air from assembly (Unnecessary if lens assembly is filled under vacuum).
Step 10: Mount assembly in place.

In one embodiment, the dog bone shape may comprise a center rectangular region; a left taper region, connected with the left side of the center rectangular region, wherein a height of the region increases symmetrically from the left side of the center rectangular region to a left side of the left taper region by tracing along a first pair of ellipses which are offset from the center axis by a first offset distance; a left end region, connected with the left side of the left taper region, wherein a height of the region symmetrically increases, reaches a maximum, and decreases by tracing along a second pair of ellipses which are offset from the center axis by a second offset distance; a right taper region, connected with the right side of the center rectangular region, wherein a height of the region increases symmetrically from the right side of the center rectangular region to a right side of the right taper region by tracing along a third pair of ellipses which are offset from the center axis by the first offset distance; and a right end region, connected with the right side of the right taper region, wherein a height of the region symmetrically increases, reaches a maximum, and decreases by tracing along a fourth pair of ellipses which are offset from the center axis by the second offset distance.

In some embodiments, the tunable fluidic cylindrical lenses of the present invention may be used for beam-shaping applications. Edge-emitting laser diodes emit elliptical beams with both axes (fast axis and slow axis) diverging, but at different angles. As a non-limiting example, the two tunable fluidic cylindrical lenses may be used to circularize the output of diodes (such as edge-emitting laser diodes) and other lasers. The cylindrical lens pair may be used to expand the narrow dimension of the beam, which corresponds to the slow axis, by arranging the two lenses in series and tuning the focal lengths of the two lenses. A three lens system with a tunable circular lens and two tunable cylindrical lenses may provide for automated focusing and beam-shaping. With traditional glass optics, the focal lengths of the lenses are fixed, and it is necessary to try to match the focal length to circularize the beam. The fluidic cylindrical lenses of the present invention provide for tunable control of the focal length and thus, better performance. Other applications may include machine vision, microscopy, laser processing, ophthalmology, medical imaging, projection, augmented reality, photography, automotive sensors, and other precision optical applications. The fluidic lenses of the present invention may be added to an optical microscope to provide automated focus and astigmatism correction. The focusing (spherical) lens may be used to cross section the image along the optical axis to generate a three dimensional image of the sample. The cylindrical lens or lenses may be used to correct for aberrations introduced during the propagation of the light through the sample medium or in vitro liquids. The lens system may also be integrated into the light source of an inverted microscope to correct for any aberrations in the illumination system. Furthermore, the cylindrical lens may be used to generate a "line" illumination system source.

Example

The following is a non-limiting example of the present invention. It is to be understood that said example is not intended to limit the present invention in any way. Equivalents or substitutes are within the scope of the present invention.

Figure 24:
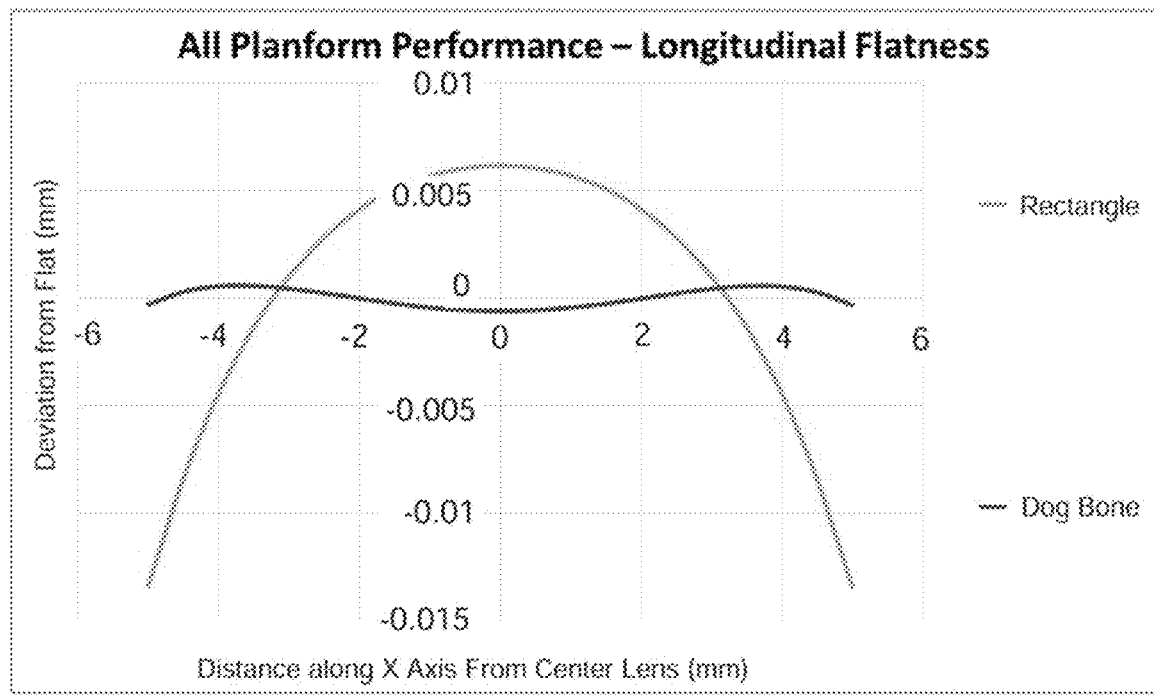
FIG. 24 shows a plot along the longitudinal axis (long axis) of the results of the finite element analysis of a rectangular cylindrical lens and an optimized dog bone cylindrical lens. The dog bone shaped lens shows significantly improved performance than the cylindrical shaped lens.

Parametric Dog Bone Geometry for the Cylindrical Fluidic Lens:

The present example features a dog bone shape with a geometry that deviates from a rectangle by extending each of the four corners using two auxiliary circles (a total of eight auxiliary circles, symmetrically arranged in pairs for each corner). As shown in FIG. 24, this shape enables the fabrication of cylindrical fluidic lenses with minimized or no defocus, without the need to extend the length of the lens. This design has seven parameters that may be tuned to form a dog bone shape with different dimensions. The length (l) and the width (w) of the initial rectangle are set initially. The present example uses a 3:1 ratio of length over width to obtain a cylindrical lens structure after positive or negative pressure is applied. Other ratios may also be used. Two auxiliary circles, with radii $r^1$ and $r^2$ ($r^1$ and $r^2$ may be the same or different) are respectively used to determine the inward and outward radii of curvature for the dog bone shape. Each circle may also be replaced with an ellipse, with the height to width ratios could be described by the parameters $e^1$ and $e^2$. Finally, an additional value (h) could be added to offset the vertical positioning of the auxiliary circles and thus increase the length of the dog bone structure towards the y-axis.

Basic Dog Bone Geometry Using Two Auxiliary Circles:

This design uses two circles for determining the inward and the outward curvature of the dog bone shape. FIG. 1 shows the resulting structure. First, three consecutive sections (or regions along the x-axis) of the shape are defined. Second, the value of the y dimension of the dog bone shape is calculated in the positive x domain for each of the three sections. The limitations of the three sections along the x-axis are:

I) $x < \frac{l}{2} - r1 - 2r2$ (flat region)

II) $\frac{l}{2} - r1 - 2r2 < x < \frac{l}{2} - 2r2$ (inward curve)

III) $x > \frac{l}{2} - 2r2$ (outward curve)

According to this separation, y=f(x) is calculated with the equation below, according to the x as:

I) $y = \frac{w}{2}$ (1)

II) $y = w/2 + r1 - \sqrt{r1^2 - (x - (l/2 - 2r2 - r1))^2}$

III) $y = h + w/2 + r1 + \sqrt{r2^2 - (x - (l/2 - r2))^2}$

Once the x and the corresponding y values are calculated for the positive x domain, the other domains where x and y may be negative are extrapolated using the symmetry across the x and y axes, to obtain the full shape of the dog bone cylindrical lens.

Figure 2:
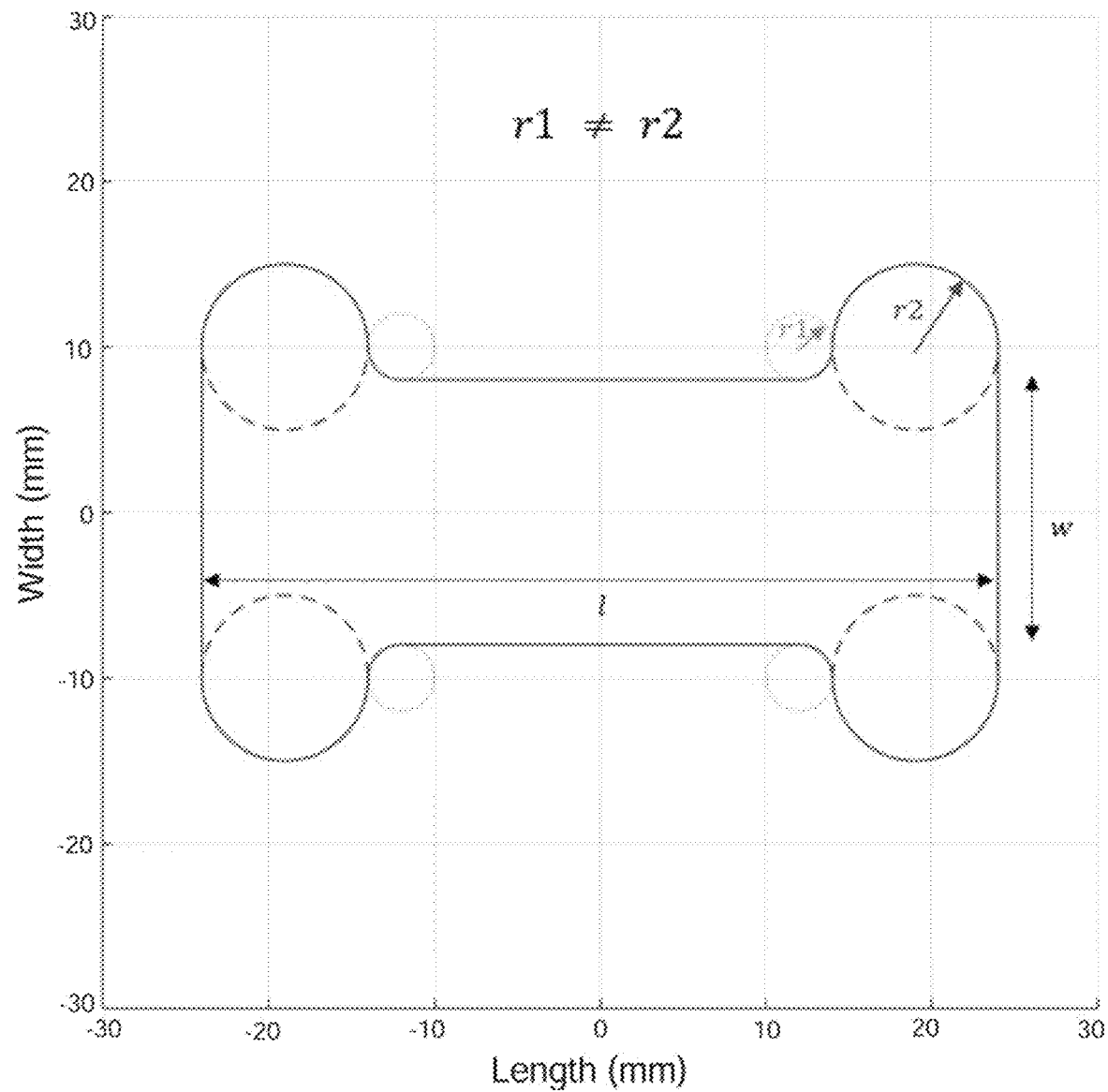
FIG. 2 shows a parametric dog bone design of the present invention that has two auxiliary circles with different radii in each corner.

These equations are sufficient to describe many possible dog bone geometries that exploit two circular auxiliary circles. An example of dog bone shape with two circles have different radii is shown in FIG. 2. The amount of the spherical contribution in the cylindrical tunable lens will depend on the combination of the five parameters (l, w, r1, r2, and h) that is used in generating the model. Using these equations, it has been determined theoretically and experimentally that the dog bone cylindrical lens with the relations between parameters such that the aspect ratio of the rectangle (l/w) equals 3, r1/r2 equals 1, r1/w is about 0.2, and h equals 0 exhibits nearly pure cylindrical characteristics. As such, lenses with proportional dimensions should also have the same characteristics.

Extended parametric dog bone cylindrical lens geometry by adding ellipticity: The parametric dog bone design is not limited to auxiliary circles, but could also use auxiliary ellipses instead. Using ellipses, it may be possible to achieve even finer tuning of the cylindrical lens characteristics, and further reduction of the spherical contribution. This is accomplished by introducing two separate ellipticity coefficients (e1 and e2) for the two auxiliary circles. The ellipticity coefficients are the ratio of the vertical radius of each ellipse to the horizontal radius. The equations are therefore slightly modified, considering the same x domains such that:

$y = w/2$      I)

$y = w/2 + e1r1 - e1\sqrt{r1^2 - (x - (l/2 - 2r2 - r1))^2}$      II)

$y = h + w/2 + e1r1 + e2\sqrt{r2^2 - (x - (l/2 - r2))^2}$      III) (2)

Figure 3:
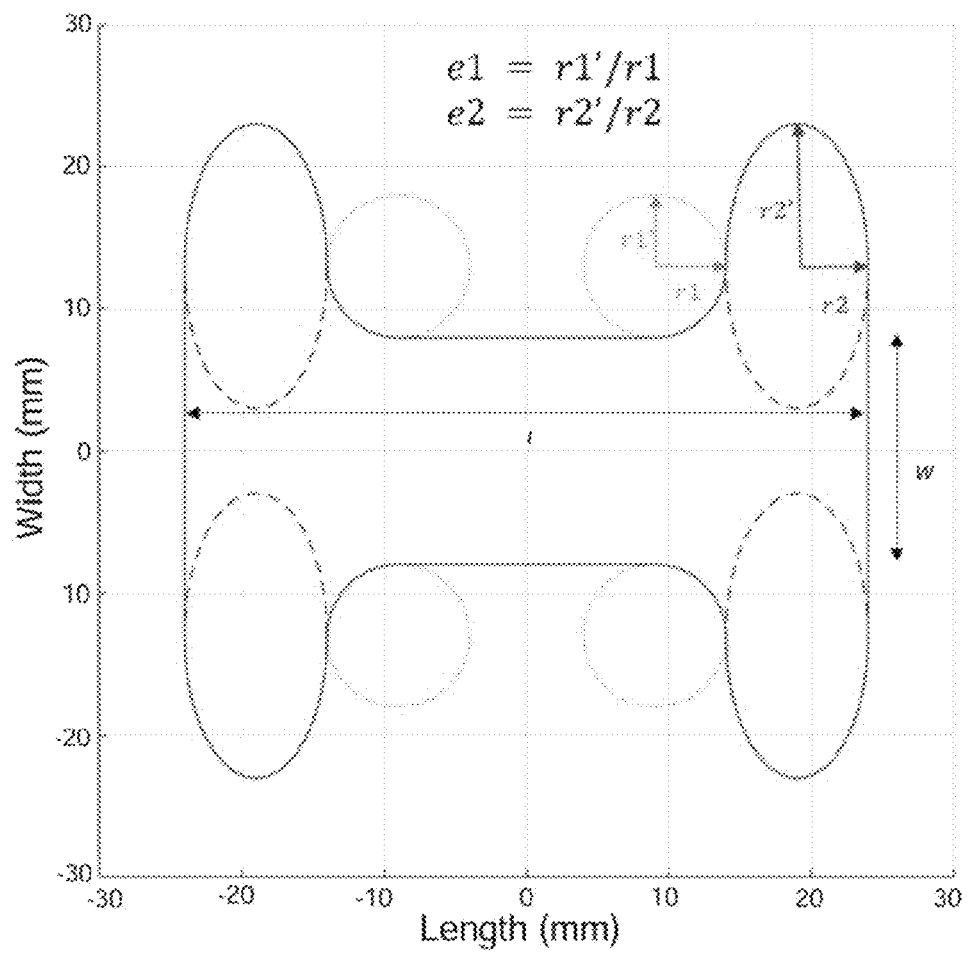
FIG. 3 shows a parametric dog bone design that uses non-circular ellipses. Such designs may enable further tuning of the cylindrical lens characteristics and reduction of the spherical contribution. The ellipticity of the lenses are parametrized using e1 and e2.

The resulting dog bone shape is demonstrated in FIG. 3. In this particular example, the first auxiliary ellipse is a circle, while the second is not. Using the extended parametric dog bone shape equations, it is possible to design cylindrical lenses that have desired characteristics, particularly minimum defocus contribution. Circular or elliptical shapes may be used to determine the curvature characteristics of the dog bone, and different parameters could be evaluated using the equations formulated here systematically.

In some embodiments, the dog bone shapes of the present invention may be defined using curves other than elliptical curves. As a non-limiting example, the curves may be represented mathematically by trigonometric functions, Bessel functions, piecewise polynomials, splines, exponential curves, or hyperbolic curves or combinations of various mathematical functions.

Figure 4A:
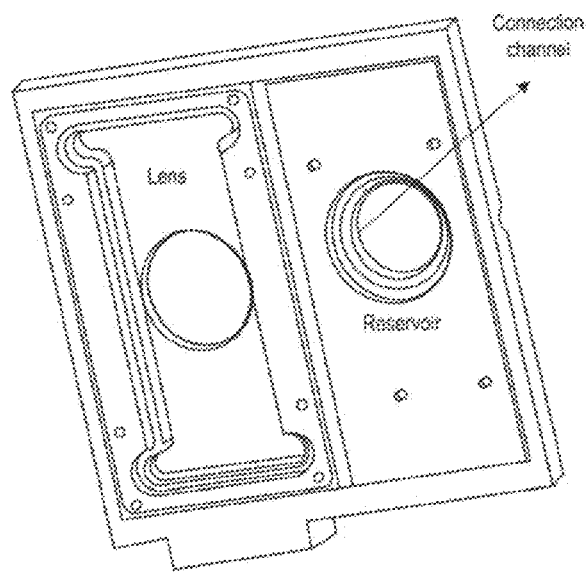
FIGS. 4A-4B show examples of the assembly of dog bone shaped cylindrical lenses.
Figure 4B:
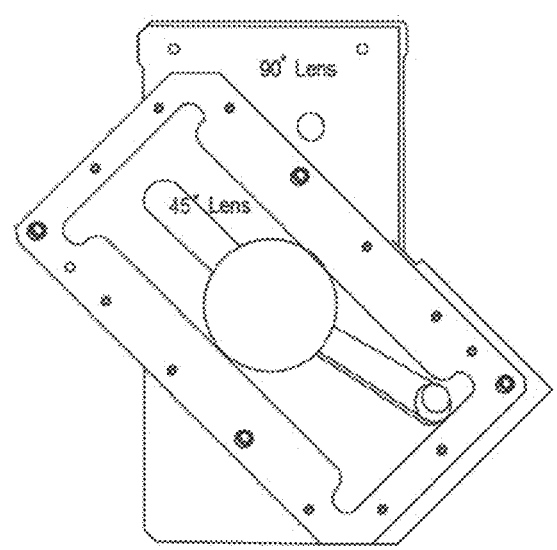
Figure 5A:
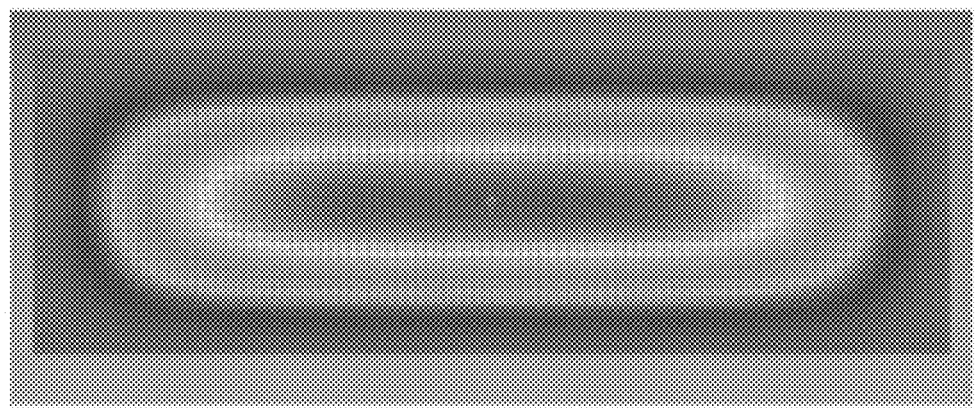
FIGS. 5A-5C show examples of cylindrical lens platforms evaluated.
Figure 5B:
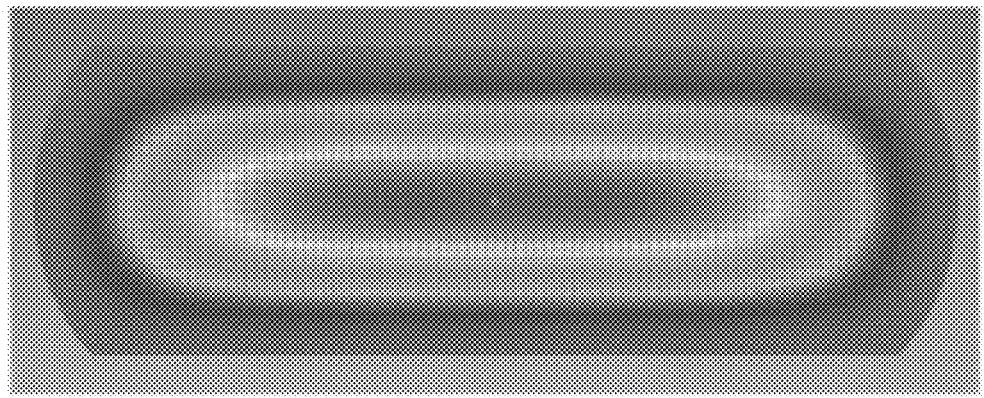
Figure 5C:
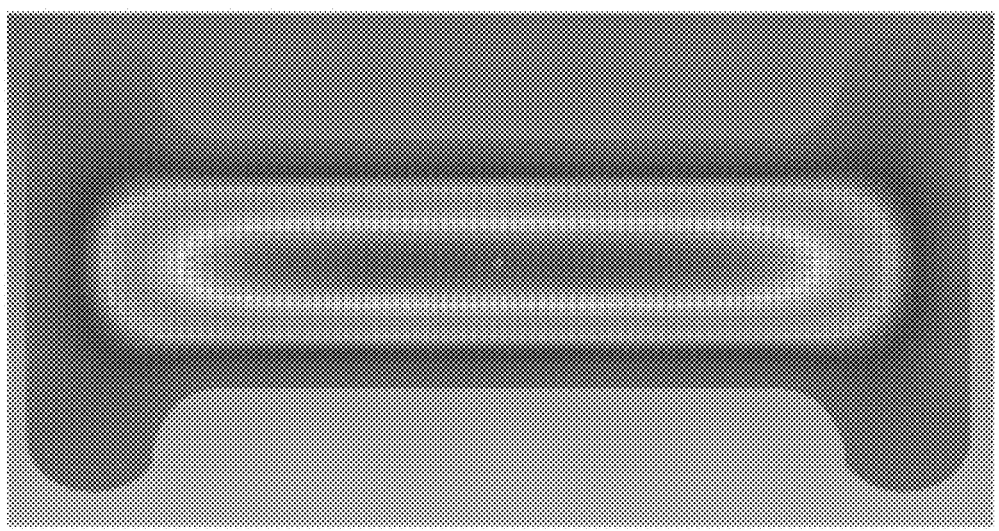
Figure 6A:
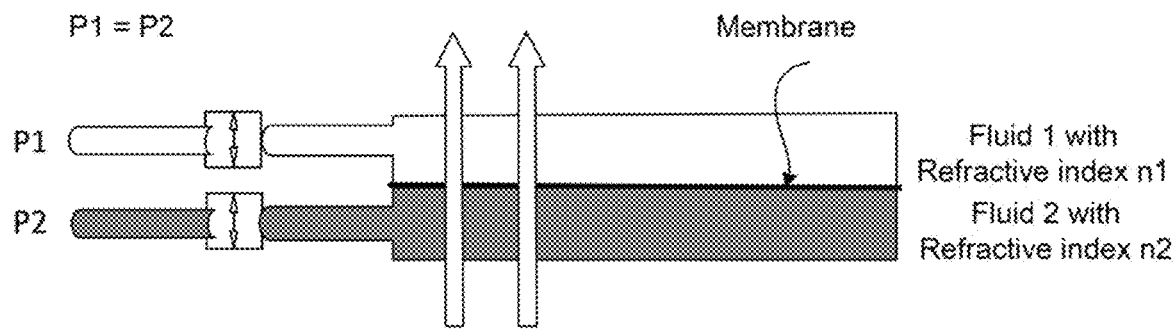
FIGS. 6A-6C show side view illustrations of a two fluid lens which has a fluid on either side of the deformable membrane. In these figures, Fluid 2 has the higher refractive index, if Fluid 1 had the higher index, the light propagation would be different and the converging and diverging rays would swap in FIGS. 6B and 6C. The relative pressures of the two fluids (P1 and P2) determine the degree of curvature of the deformable membrane. Light passing through the lens from the top or bottom of the illustration may converge or diverge depending on the shape of the membrane and the relative refractive indexes of the two fluids.
Figure 6B:
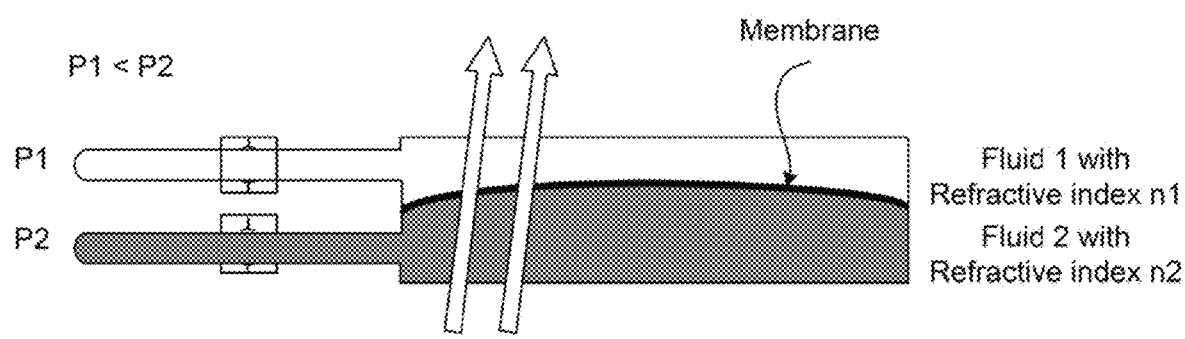
Figure 6C:
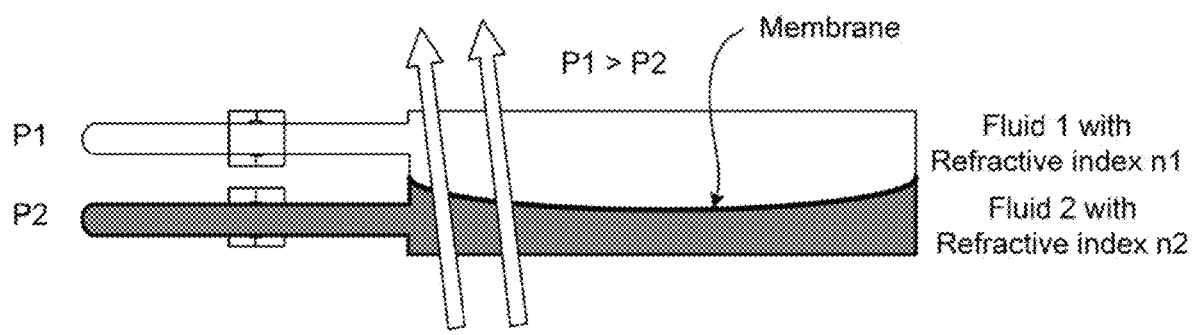
Figure 9:
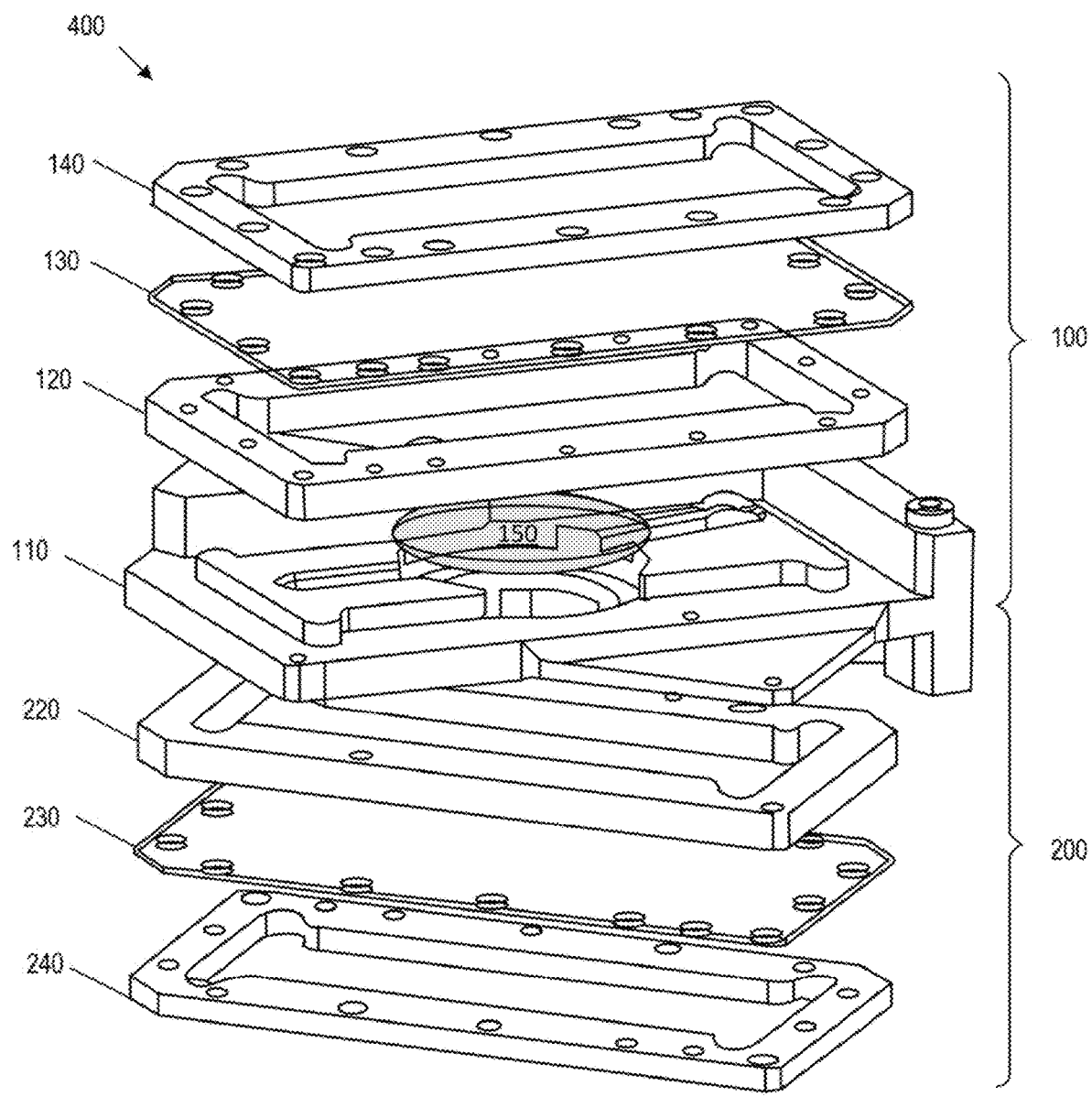
FIG. 9 shows an exploded view illustration of a fluidic lens assembly of the present invention, having two cylindrical fluid lenses offset by 45 degrees.
Figure 10:
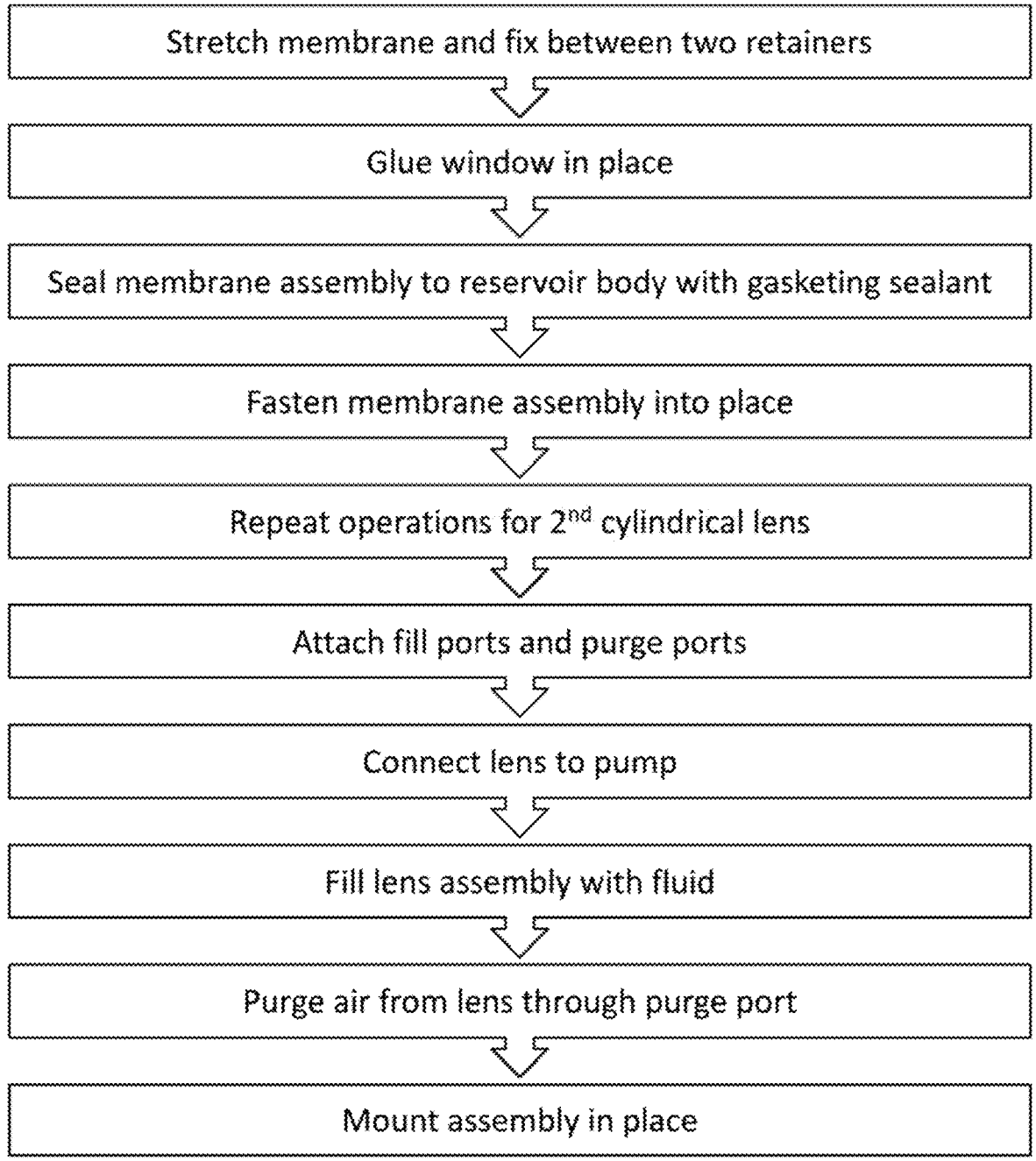
FIG. 10 shows a flow chart describing a method for fabricating a fluidic lens assembly of the present invention.
Figure 11:
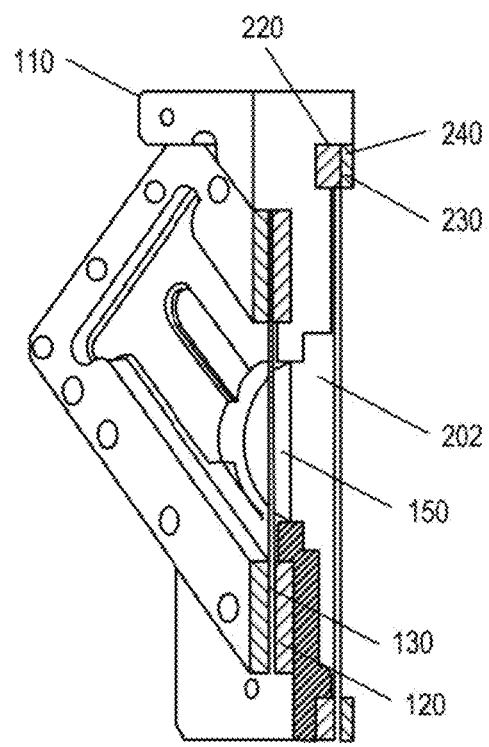
FIG. 11 shows a cross-sectional view illustration of a fluidic lens assembly of the present invention.
Figure 12:
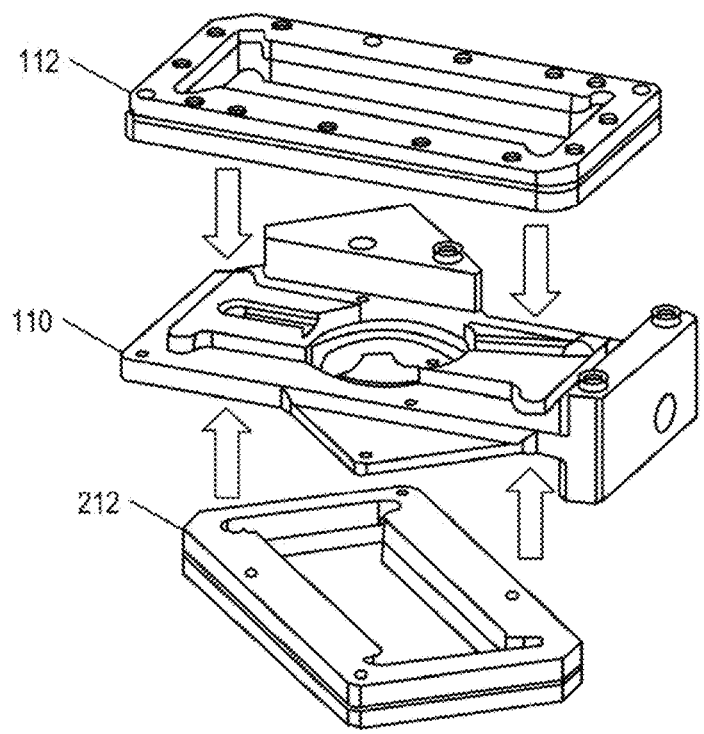
FIG. 12 shows an illustration of the positioning of two membrane assemblies on a reservoir body with a shared rigid internal window between the two cylindrical fluidic lenses.
Figure 13:
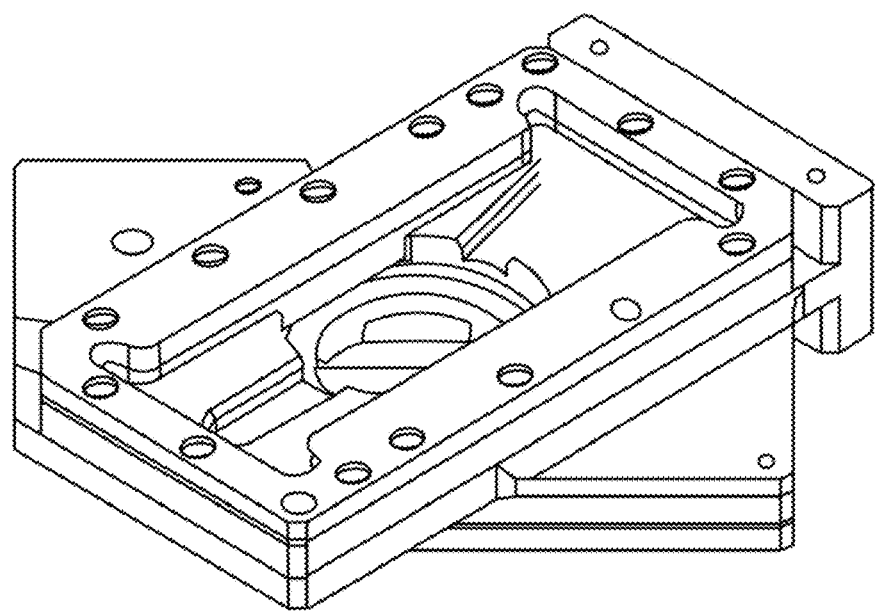
FIG. 13 shows an illustration of the two cylindrical fluidic lenses shown in FIG. 12, after the membrane assemblies are fixed in position.
Figure 14:
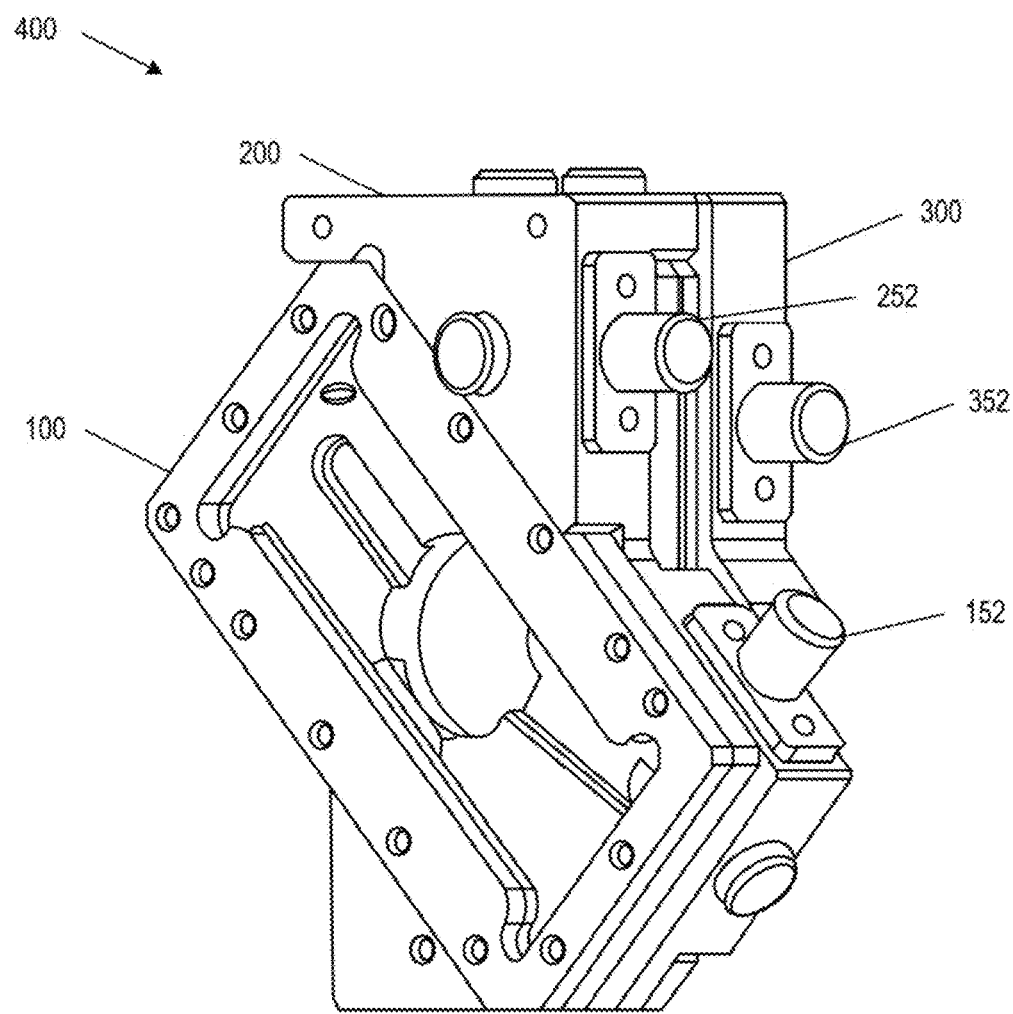
FIG. 14 shows an illustration of a fluidic lens assembly having two offset cylindrical lenses and a spherical fluidic lens, all aligned with a common optical path through the lenses.
Figure 15:
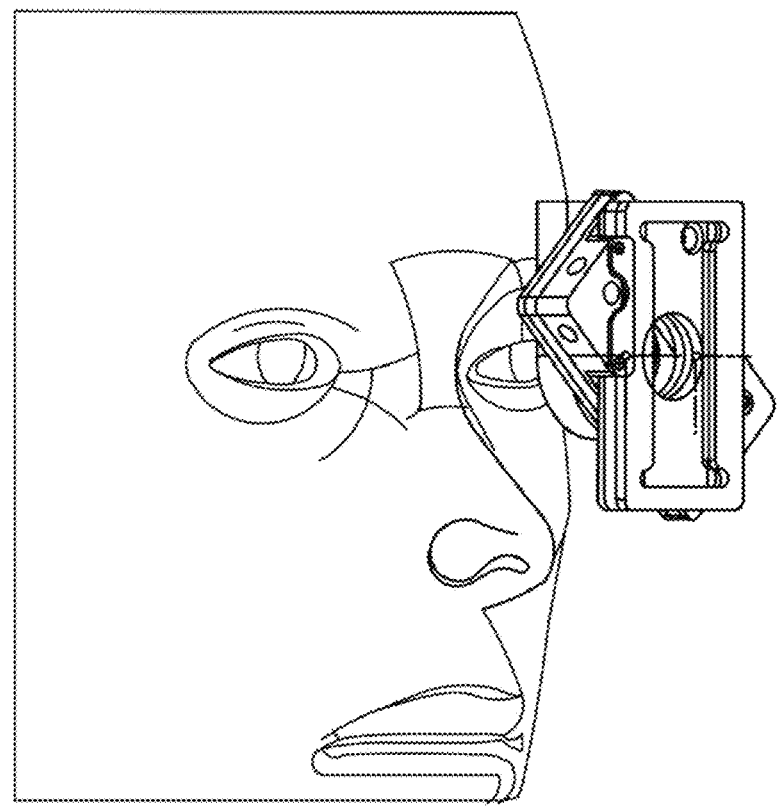
FIG. 15 shows an illustration of the positioning of a fluidic lens assembly of the present invention in relation to the eye of a user. The offset angle of the second cylindrical fluidic lens from the first (vertical) cylindrical fluidic lens is shown to provide for ergonomic fit around the nose of the user.
Figure 16:
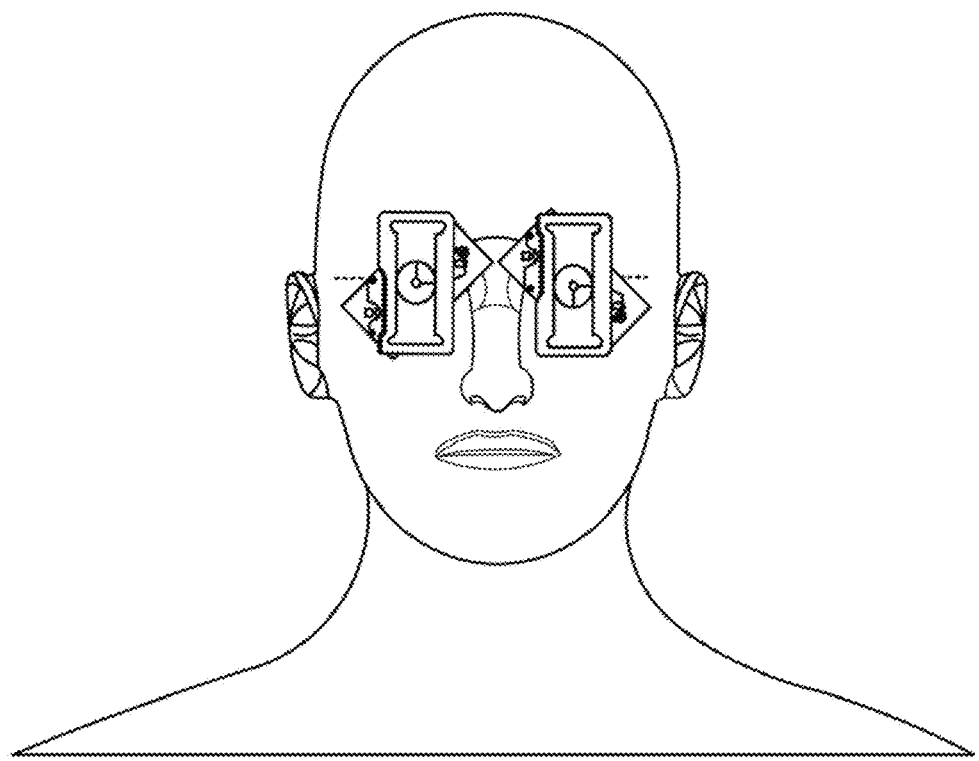
FIG. 16 shows an illustration of the positioning of a pair of fluidic lens assemblies in relation to the left and right eyes of the user. As illustrated, the left and right fluidic lens assemblies are mirror image versions of each other.
Figure 17:
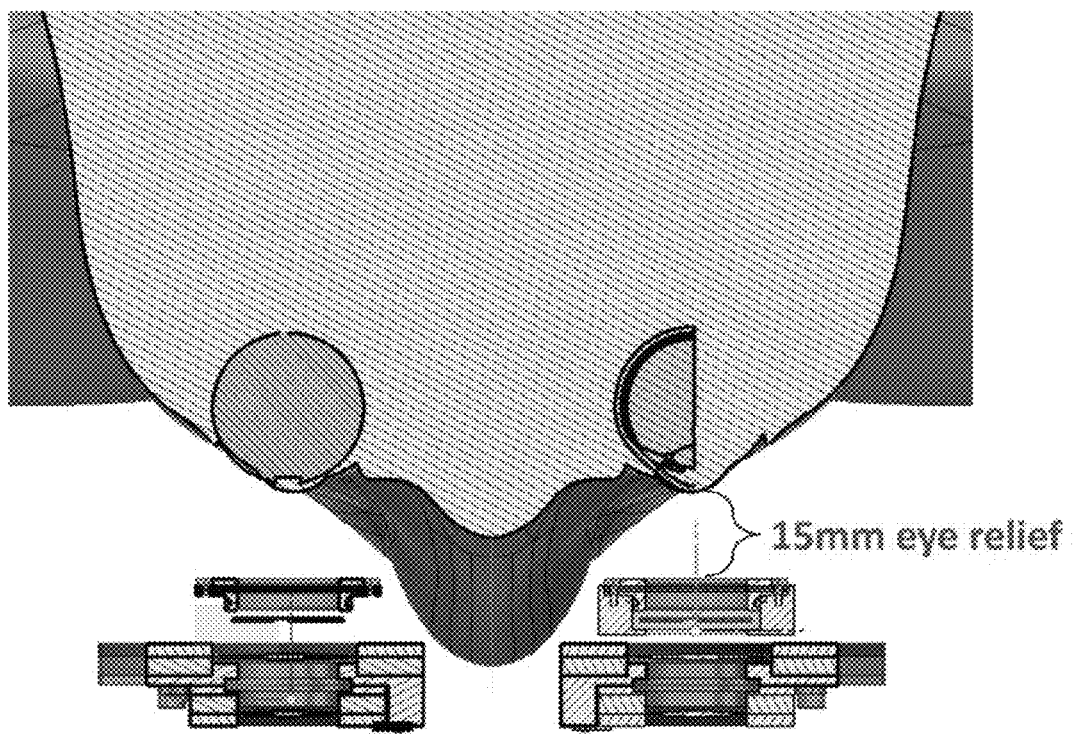
FIG. 17 shows a top down illustration of the positioning of a pair of fluidic lens assemblies in relation to the left and right eyes of the user.
Figure 18:
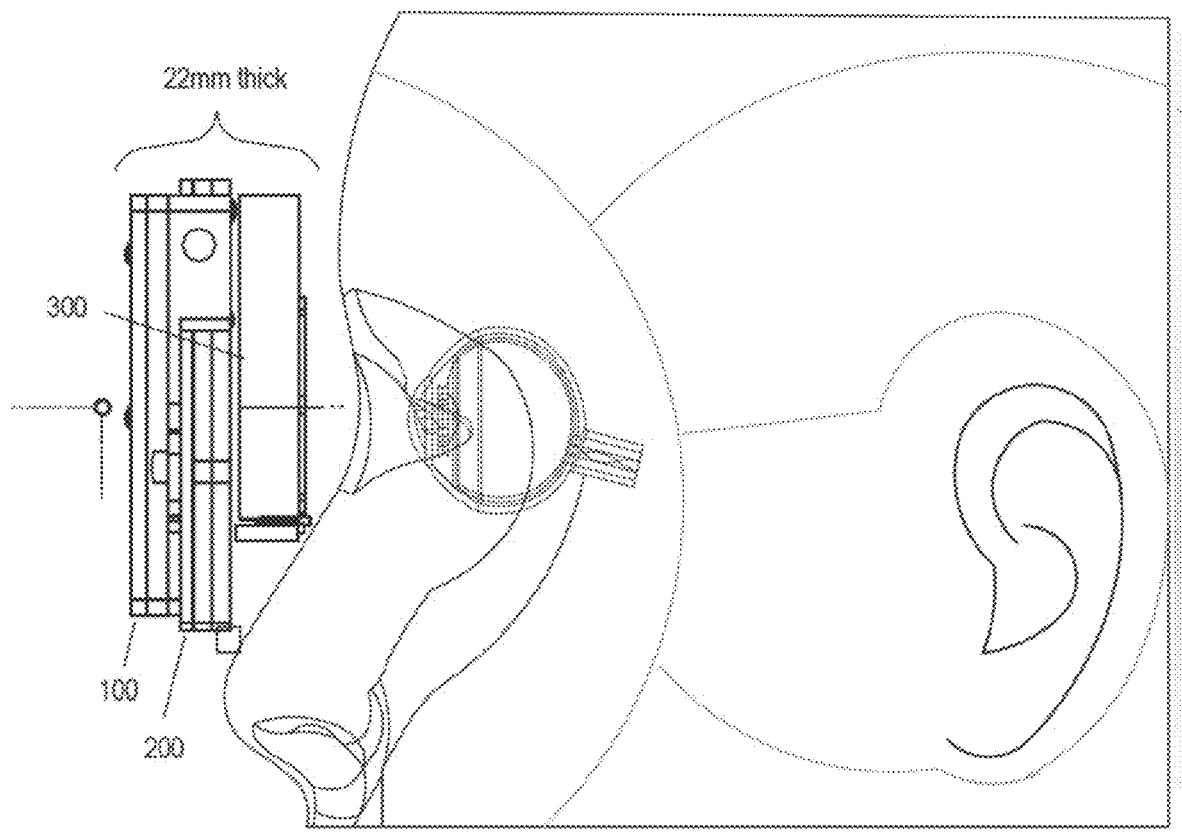
FIG. 18 shows a side view illustration of the positioning of a fluidic lens assembly in relation to the left eye of the user.
Figure 20:
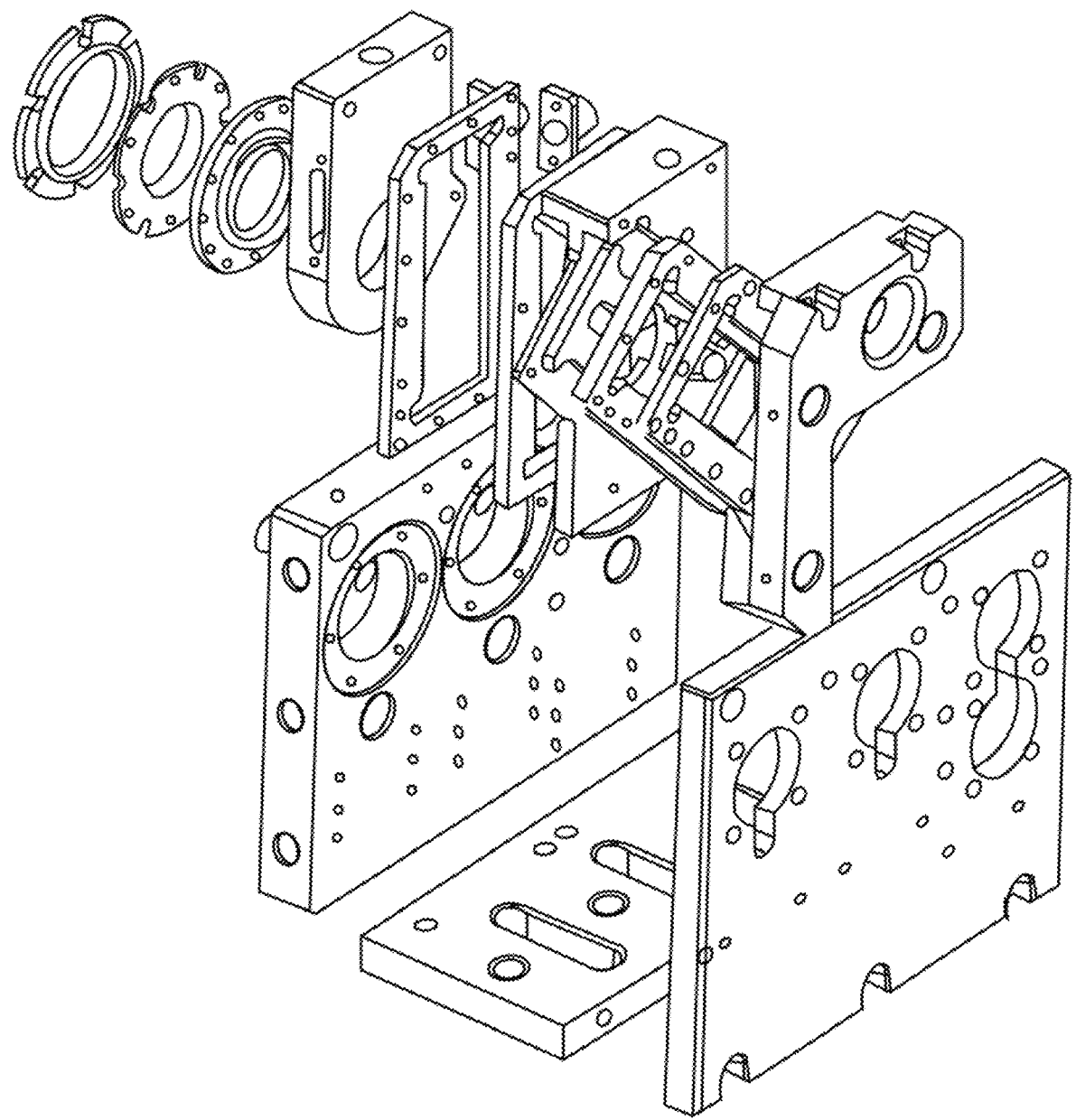
FIG. 20 shows an exploded view illustration of a fluidic lens assembly of the present invention. In addition to the spherical fluidic lens and two cylindrical fluidic lenses, this figure shows a diaphragm pump assembly for controlling the fluid pressure in each lens.
Figures 21, 22:
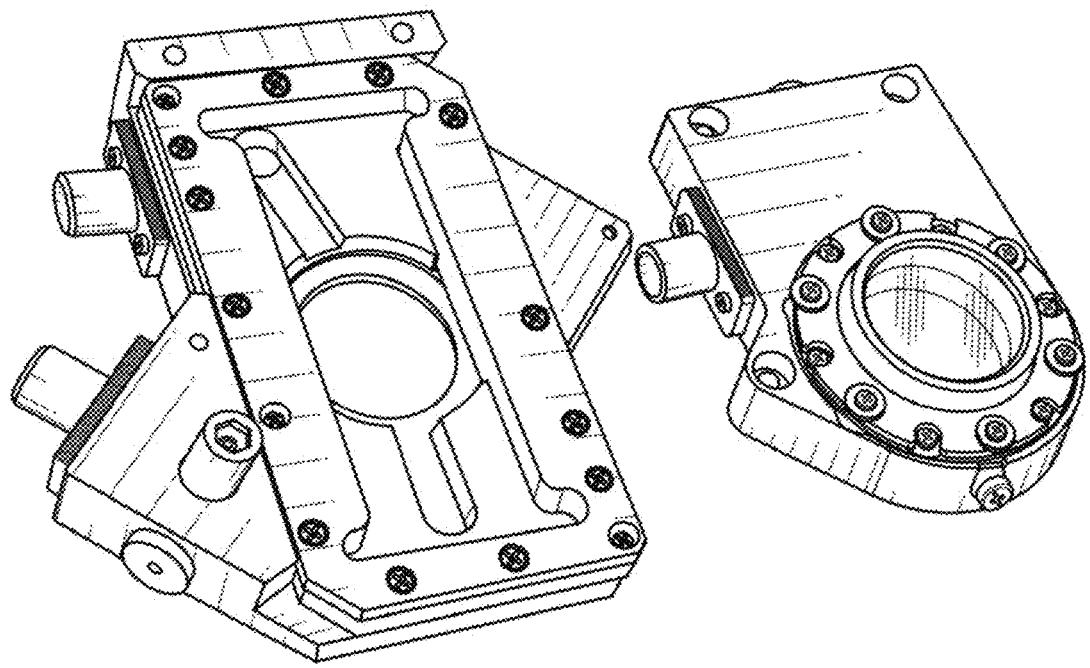
FIG. 21 shows a perspective view illustration of a partially disassembled fluidic lens assembly of the present invention with two offset cylindrical fluidic lenses, alongside a spherical fluidic lens.
FIG. 22 shows a table of relevant specifications for various fluids which may be used in the fluidic lenses of the present invention.
Figure 23:
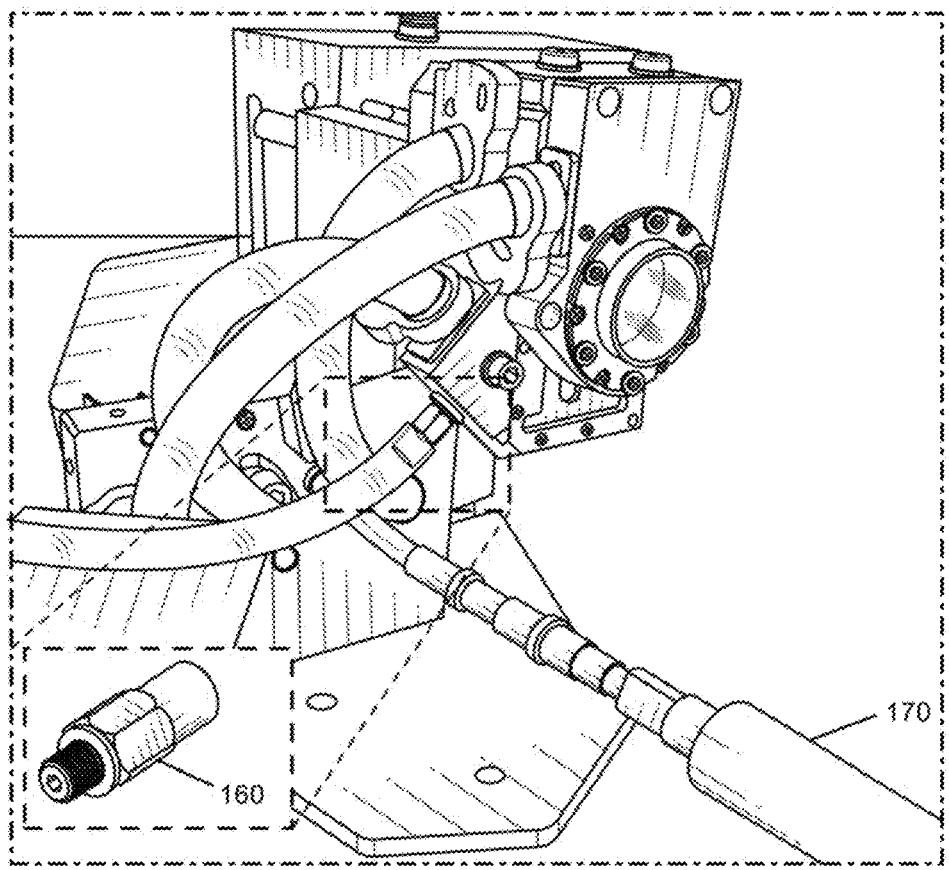
FIG. 23 shows a perspective view illustration of a fluidic lens assembly with fluidic hoses attached to fill ports and purge ports of the lenses so as to allow for filling of the assembly with fluid and the removal of air from the system. In this example, a simple syringe is used as the fill pump.

Dog bone cylindrical fluidic lens fabrication: The dog bone cylindrical lenses of the present invention may be fabricated via methods which are similar those which are used to fabricate spherical tunable fluidic lenses. In another embodiment, the lens design may include modifications result in a separate fluid reservoir, away from the fluidic chamber, which is connected with the fluidic chamber of the fluidic lens via connectors such as tubes. Each single lens may include a flexible membrane of various transparent materials. As a non-limiting example, the transparent material may be silicone, polydimethylsiloxane (PDMS), Mylar, polycarbonate, polyvinyl, or another polymer material. This flexible membrane may be sandwiched by a compartment and a dog bone shaped frame. As a non-limiting example, the dog bone geometrical shape may be defined by the aforementioned parametric equation. In some embodiments, the optical lens also includes a transparent optical window across from the flexible membrane. In some embodiments, two cylindrical lenses may be stacked on top of each other, either sharing or not sharing a single transparent optical window. In one embodiment the lenses may be offset by an angle of about 45° so as to correct for any angle of astigmatism. Two possible methods to assemble the cylindrical fluidic lens or lenses, are illustrated in FIGS. 4A-B. In some embodiments, the fluid reservoir may be in the same unit as the tunable lens. In other embodiments, the fluid reservoir may be a separate unit which is connected with the fluidic chamber of the fluidic lens via connectors such as tubes.

The fluid selection within the lens depends on the application and the desired refractive index. Additionally, material incompatibilities should be taken into account. In some embodiments, the fluid may have low viscosity and high transparency, cause little or no scattering, and be chemically inert. Non-limiting examples of suitable fluids include water, glycerol, dimethylsulfoxide, silicone oil, ethanol, methanol, isopropanol, acetone, aqueous solutions of ions and organic compounds, mineral oil, index matching fluids, and silicone oils.

As used herein, the term "about" refers to plus or minus 10% of the referenced number.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting essentially of" or "consisting of", and as such the written description requirement for claiming one or more embodiments of the present invention using the phrase "consisting essentially of" or "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A phoropter having a line of sight for a viewer to see an eye chart, the phoropter comprising:
   a. a tunable defocus lens in the line of sight;
   b. a first tunable astigmatic lens in the line of sight, the first tunable astigmatic lens having a first cylindrical axis; and
   c. a second tunable astigmatic lens in the line of sight, the second tunable astigmatic lens having a second cylindrical axis which is offset by an offset angle from the first cylindrical axis;
   wherein each of the tunable astigmatic lenses lacks spherical defocus;
   wherein each of the tunable astigmatic lenses comprises a fluidic lens comprising:
   a. a fluidic chamber with a dog bone shaped opening, wherein the dog bone shape comprises:
      i. a center rectangular region, having a constant width, a constant height, and a center axis running from a left side of the center rectangular region to a right side of the center rectangular region;
      ii. a left end region, connected with the left side of the center rectangular region, having a maximum height that is greater than the height of the center rectangular region; and
      iii. a right end region, connected with the right side of the center rectangular region, having a maximum height that is greater than the height of the center rectangular region; and
   b. a flexible transparent membrane attached to the fluidic chamber and covering the opening;
   wherein change of the fluid pressure within the fluidic chamber changes the deformation of the flexible transparent membrane and thus the power of the tunable astigmatic lens.

* * * * *